United States Patent [19]

Norton et al.

[11] Patent Number: 4,613,323

[45] Date of Patent: Sep. 23, 1986

[54] MULTIPLE FUNCTION INTUBATION APPARATUS AND METHOD

[75] Inventors: Jane A. Norton; Diana L. Twyman; A. Byron Young; Robert Rapp, all of Lexington, Ky.

[73] Assignee: University of Kentucky Research Foundation, Lexington, Ky.

[21] Appl. No.: 672,414

[22] Filed: Nov. 19, 1984

[51] Int. Cl.$^4$ ............................................. A61M 25/00
[52] U.S. Cl. ....................................... 604/43; 604/54; 604/270
[58] Field of Search .................. 604/54, 43, 49, 40, 604/77, 264, 270, 280; 128/207.14

[56] References Cited

U.S. PATENT DOCUMENTS

| | | |
|---|---|---|
| 1,211,928 | 1/1917 | Fisher ........................... 604/40 |
| 2,614,563 | 10/1952 | Devine, Jr. . |
| 2,930,378 | 3/1960 | Buyers . |
| 3,426,759 | 2/1969 | Smith . |
| 3,774,608 | 11/1973 | Wohler, Jr. ................. 604/264 X |
| 4,300,550 | 11/1981 | Gandi et al. . |
| 4,385,631 | 5/1983 | Uthmann ........................ 604/43 |
| 4,406,656 | 9/1983 | Hattler et al. . |
| 4,410,320 | 10/1983 | Dykstra ......................... 604/270 |
| 4,469,483 | 9/1984 | Becker et al. ................. 604/280 |

Primary Examiner—Stephen C. Pellegrino
Attorney, Agent, or Firm—King and Schickli

[57] ABSTRACT

An apparatus and its method of use are provided allowing lavage, sump and enteral feeding operations with only one intubation. The apparatus includes a first tube having two distinct passageways. One of these passageways completely contains a second, feeding tube during intubation. Once the first tube is in place in the patient, the second tube is extended from the first tube so as to enter the stomach. The extension of the second tube opens ports in the first passageway of the first tube, thereby allowing sump or lavage treatment with the second passageway of the first tube serving as an air vent. A constriction in the end of the first passageway engages a band on the proximal end of the second tube to keep the tubes together. Once gastric emptying of the patient resumes, the second tube immediately moves into the duodenum then into the jejunum past the Ligament of Treitz and the first tube is withdrawn from the patient while maintaining the second tube in position for enteral feeding through feeding ports in its distal end.

10 Claims, 8 Drawing Figures

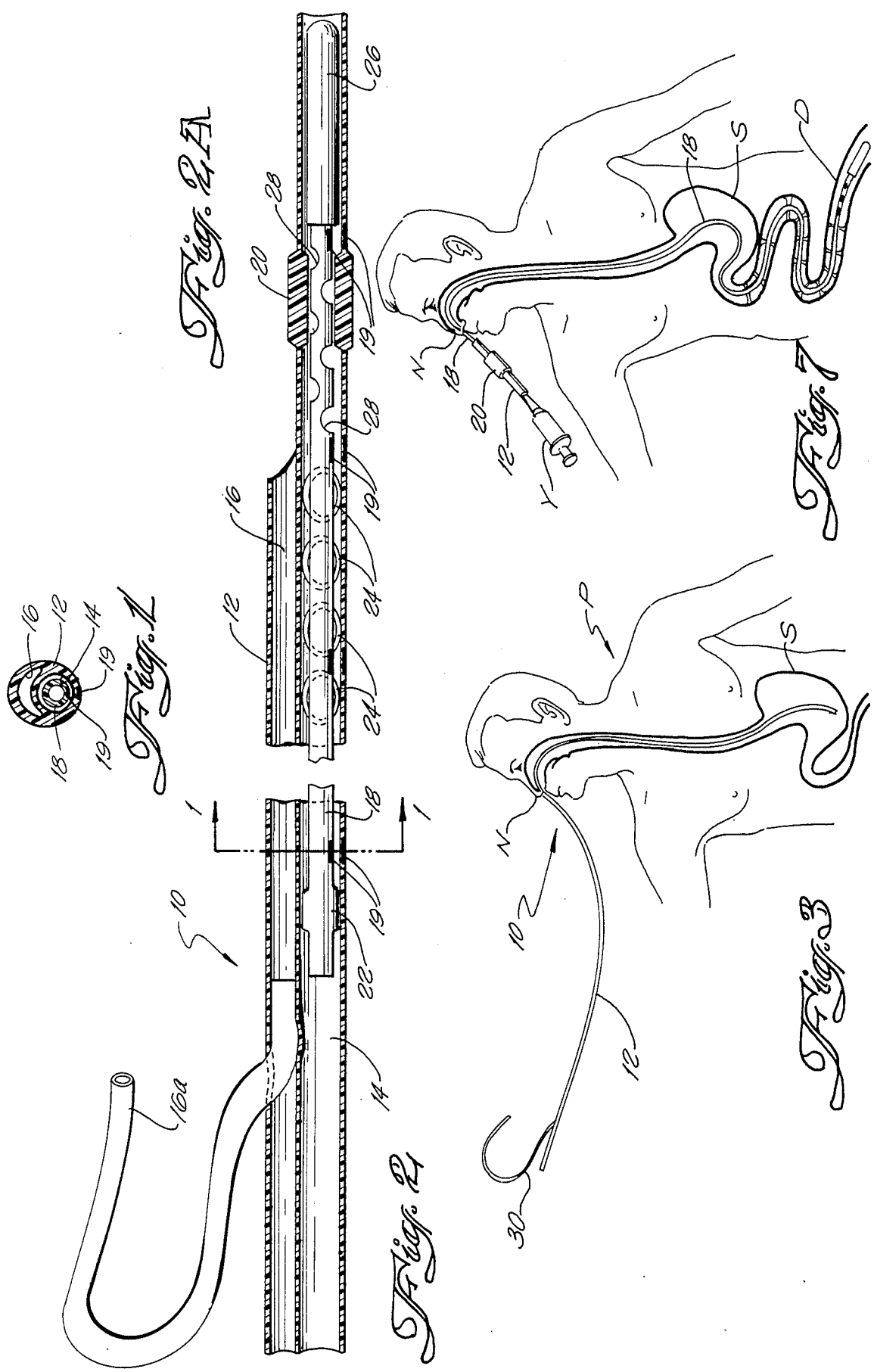

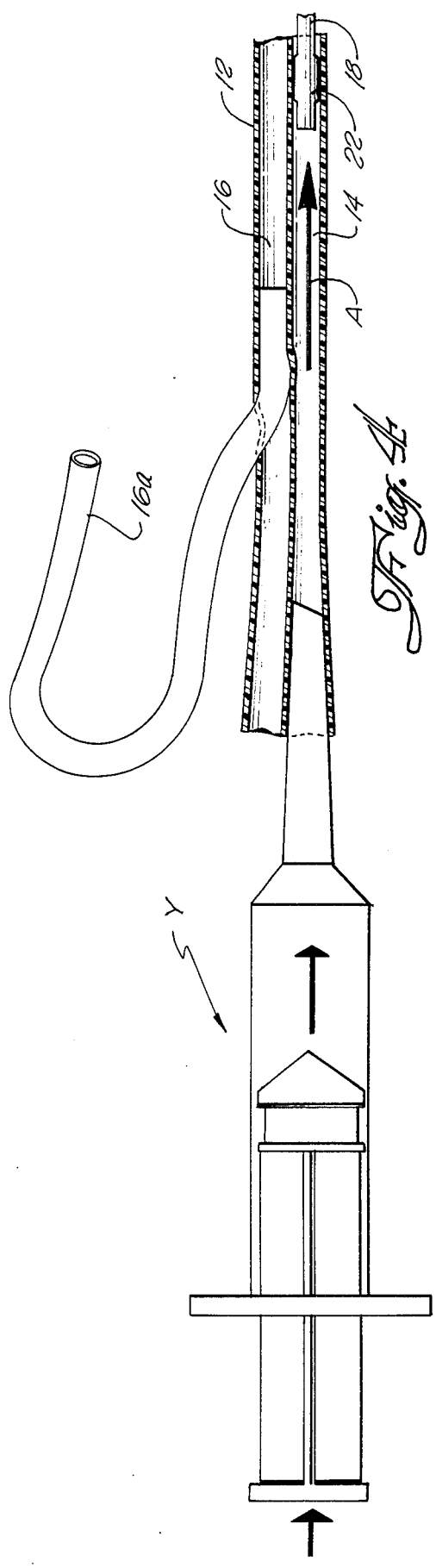
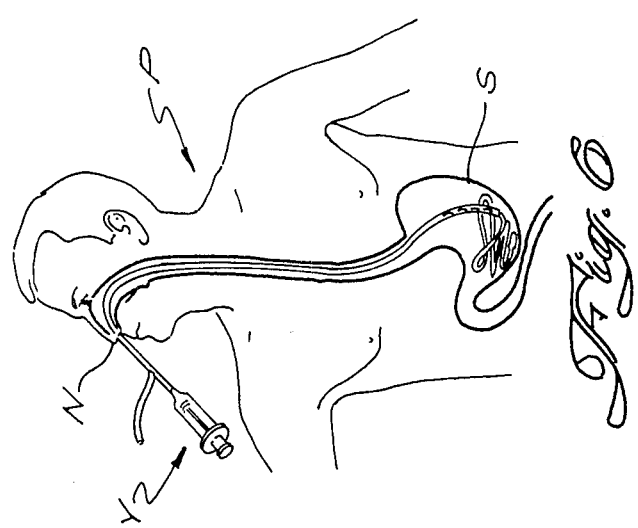
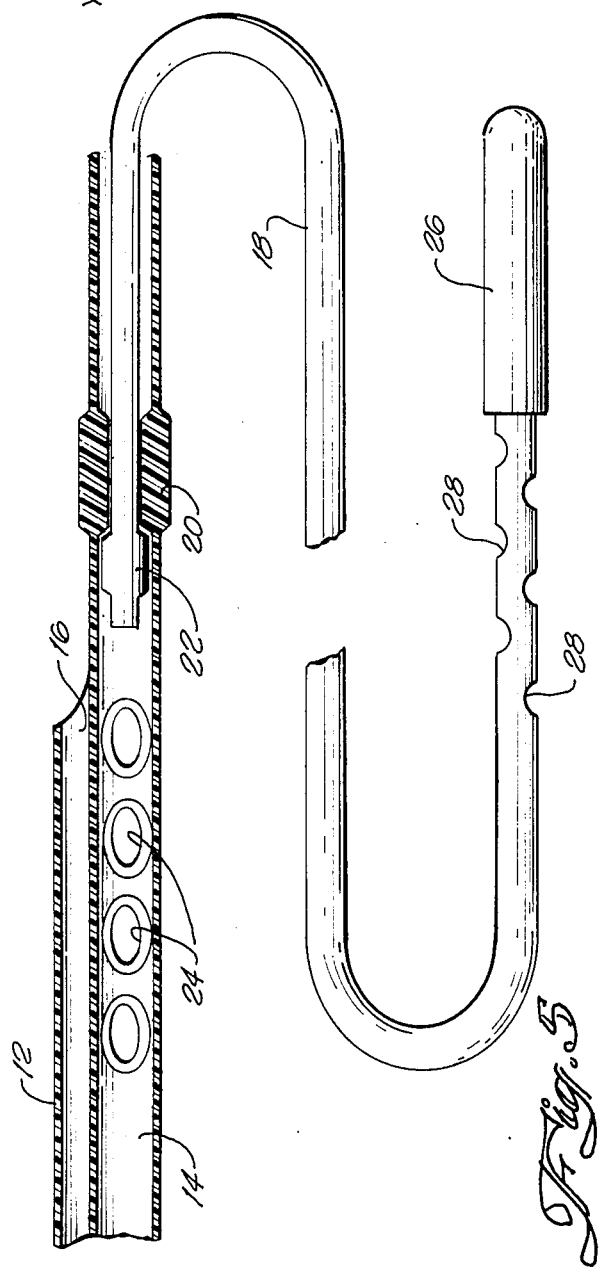

MULTIPLE FUNCTION INTUBATION APPARATUS AND METHOD

TECHNICAL FIELD

The present invention relates generally to medical apparatus and, more particularly, to an intubation apparatus providing potential lavage, sump and enteral feeding functions for a patient with only a single intubation and the related method.

BACKGROUND ART

Severe injury and major operation often lead to traumatized, even multiple traumatized patients. In treating such patients, a general anesthesia is generally used. During such an operation, the intestines of the patient may be put to sleep and result in paralytic ileus, or paralysis of the bowel. It is also not uncommon for a severe injury, such as a head injury received in an automobile accident, to involve a disruption of the gastric emptying function of the patient.

In either or a combination of the above events, the decrease or loss of function makes it necessary for purposes of effective treatment and patient safety, to decompress the stomach of the patient and begin a sump operation within a short time, and maintain the stomach in that state until gastric emptying renews and stabilizes. Also, at times the best treatment calls for a lavage operation by introduction of a cleansing solution to help remove material from the stomach. In order to achieve the emptying and/or cleansing of the stomach, it is standard medical practice to intubate the patient with a sump/vent tube. As shown in U.S. Pat. No. 2,614,563 to Devine, Jr., a tube employs air vent/suction for providing an effective pressure equalization and drain of the stomach and includes two separate passageways to do this. Specifically, the first passageway acts as an air vent or in-flow lumen, while suction is applied to the second passageway. The introduction of the air through the first passageway is essential to the employing of suction to empty the stomach. The air vents the stomach to ambient pressure to prevent the stomach from collapsing and the delicate sidewalls from being drawn into the opening of the suction passageway, thereby allowing efficient material passage from the stomach. To perform these functions, both passageways of the Devine device terminate in the stomach of the patient.

The decompressing and sump operations of the stomach, however, may not be the only concern for proper patient treatment. For example, it is known that caloric requirements of head-injured patients show a significant correlation with the severity of brain damage. Thus, early nutrition in severely head injured patients contributes signficantly to positive treatment.

Nutritional support in such cases has been traditionally provided by enteral feeding i.e. feeding direct into the stomach. When a conventional sump tube, as disclosed in Devine, Jr., is utilized, enteral feeding is delayed until good gastrointestinal function returns in the post injury period. Once gastrointestinal function returns in, for example, 4–8 days, it becomes necessary to remove the sump tube and proceed with a second, separate intubation of a feeding tube. Disadvantageously, this second intubation may traumatize the patient physically, as well as emotionally, if the patient is conscious or has periods of consciousness.

Further, it may be difficult if not impossible to perform the second intubation if the patient has a nasotracheal, endotracheal or tracheostomy tube. In such a case, the feeding tube may coil in the back of the patient's mouth. There is also the additional risk of doing damage to the mucous membranes in the nose and lining of the esophagus. Feeding tubes with stylets also increase the risk of inadvertent rupture of the tracheal or endotracheal cuffs. Further, feeding tubes with stylets may increase the risk of possible damage to the mucosa of the esophagus if the stylet should pass through the end or side port of the tube during intubation. Lastly, even if the second intubation is successful without any of the complications discussed above, it takes an additional period on the order of 48 hours for the normal digestive process to extend the intubated feeding tube from the stomach into the duodenum for purposes of enteral feeding. This additional delay of two days or more until nutritional support is received adversely affects the recovery, indeed the chances of survival, of the patient.

Thus, in order to provide nutritional support to patients in a shorter amount of time, other feeding methods have been proposed. One method requires surgically implanting a duodenal feeding tube in the patient. Such a procedure, however, disadvantageously exposes the already traumatized patient to additional surgery with its own trauma and risks of infection. A second alternative method involves parenteral feeding through the veins. This requires the use of a percutaneous intraclavicular subclavian vein catheter. The catheter is usually positioned in a vein in the patient's shoulder. Disadvantageously, however, this second method is very expensive, involves an increased risk of infection and is beset with other complications.

In light of the above, a need is identified for an apparatus especially adapted for post injury use to allow both a sump/lavage function and in addition an early feeding function in a single intubation. The apparatus should also provide both improved patient safety and comfort.

DISCLOSURE OF THE INVENTION

Accordingly, it is a primary object of the present invention to provide an intubation apparatus overcoming the above-identified limitations and disadvantages of the prior art of enteral feeding.

Another object of the present invention is to provide an apparatus for performing both a sump and feeding function with a single intubation.

Still another object of the present invention is to provide an apparatus and its method of use for performing three separate functions of sump, lavage and feeding for the patient with only a single intubation.

A further object of the present invention is to provide an intubation apparatus alternately allowing sump, lavage and feeding operation with only a single intubation so as to reduce patient trauma and improve patient safety and comfort.

Still a further object of the present invention is to provide an intubation apparatus wherein the feeding tube for preferred enteral feeding is extended into the stomach at the initiation of the sump function allowing the administration of early enteral nutrition to the patient post injury.

Additional objects, advantages, and other novel features of the invention will be set forth in part in the description that follows and in part will become apparent to those skilled in the art of enteral feeding upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved intubation apparatus is provided for use with seriously injured patients. Advantageously, the improved apparatus allows lavage, sump and enteral feeding functions to be provided to a patient with only a single intubation.

The intubation apparatus of the present invention includes a first or outer tube having a structure defining two separate passageways. A series of ports are provided in the first of the passageways adjacent the end of the tube that is introduced into the patient. The apparatus also includes a second or enteral feeding tube having a proximal and a distal end. The second tube is slidably received and contained within the first and larger passageway of the first tube. The first tube acts as a chute for the enteral tube. Thus, the second tube is movable between an intubation position wherein the second tube is completely contained within the first tube and an extended position wherein it extends from the first tube. The second tube is actually gently forced out of its passageway into the stomach by introducing pressurized fluid behind the proximal end. When the second tube is in the second, extended position coiled in the stomach, the series of ports in the first tube are opened. Once the ports are opened, the intubation apparatus of the present invention may function to provide sump or lavage function to the patient.

For sump operation, suction is provided to the first passageway including the series of ports. The second passageway in the first tube then acts as a vent to provide ambient pressure that prevents the tissues of the patient from collapsing and being drawn into the ports in the first tube and, thereby obstructing the passage of material from the patient.

Once extended, the second tube or enteral feeding tube is drawn from the coiled position in the stomach into the duodenum with the return of gastrointestinal function.

Both the first and second tubes include radiopaque strips that enable the viewing by x-ray of the position of the tubes within the patient. Upon confirmation that the second or feeding tube is extended into the duodenum, and the sump process is complete, the first tube may be withdrawn from the patient, and enteral feeding immediately initiated through the second tube.

Preferably, the first tube includes a constriction means, such as a ring of reduced diameter, between the porting and the distal end of the first tube. Additionally, the second tube includes engaging means adjacent the proximal end. The engaging means may comprise a band of increased diameter around the second tube. This band serves as a piston to allow the pressurized fluid to extend the second tube. When the band reaches the position of the suction ports, the first tube may be withdrawn slightly to assist in full extension. The band then engages the constriction ring of the first tube so as to retain the proximal end of the second tube within the first passageway in the fully extended position. After the sump operation is complete, as the first tube is withdrawn from the patient, the proximal end of the second tube is also withdrawn while the distal end of the second tube remains in the duodenum. After exiting the nose of the patient, the first tube may then be cut away from the proximal end of the second tube for the purposes of initiating enteral feeding through the second tube.

Preferably, the second or feeding tube may also include a weighted tip adjacent the distal end. The weighted tip aids in positioning the distal end of the extended second tube adjacent the pyloric valve of the stomach for eventual advancement into the duodenum of the patient by normal gastric function. The tip further serves to prevent aspiration of tube feeding into the trachea and lungs preventing what is known as aspiration pneumonia. This problem is of particular concern in comatose patients.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 1 is a cross-sectional view taken along line 1—1 of FIG. 2 of the intubation apparatus of the present invention;

FIG. 2 is a broken away longitudinal cross-section of the proximal end of the intubation apparatus of the present invention;

FIG. 2A is a broken away longitudinal cross-section of the distal end of the intubation apparatus of the present invention;

FIG. 3 is a schematical representation of the intubation apparatus of the present invention immediately following intubation to a patient; and showing the full length of the outer tube;

FIG. 4 is a schematical representation showing the use of a syringe to provide for pressurized fluid for extending the feeding tube of the intubation apparatus of the present invention;

FIG. 5 is a broken away view of the intubation apparatus of the present invention wherein the second or feeding tube is fully extended from the first or outer tube;

FIG. 6 is a schematical representation of the intubation apparatus of the present invention immediately following completion of the extension of the feeding tube from the outer tube (partially broken away);

FIG. 7 is a schematical representation of the intubation apparatus of the present invention following removal of the outer tube from the extended feeding tube and during initiation of enteral feeding to the patient.

Reference will now be made in detail to the present preferred embodiment of the invention, an example of which is illustrated in the accompanying drawing.

DETAILED DESCRIPTION OF THE INVENTION

Reference is now made to FIGS. 1 and 2 showing the intubation apparatus 10 of the present invention for performing lavage, sump and enteral feeding functions for a patient with only a single intubation. Since only a single intubation is required to provide these functions, there is less irritation and trauma to the already traumatized patient and, therefore, patient comfort and safety are notably improved.

As shown, the intubation apparatus 10 includes a first, outer tube 12 having dual distinct passageways 14, 16. The outer tube 12 may, for example, be made of relatively stiffer plastic for purposes of control during intubation. A second, inner relatively soft feeding tube 18 is slidably received or chuted within the first passageway 14 of the outer tube 12. The tube 12 is inserted in nose N establishing an intubation or first position in a patient P. The feeding tube 18 is completely contained within the passageway 14. As shown in FIG. 3, the proximal end is extending from the nose N and the distal end is in stomach S. The second position is where the feeding tube extends from the outer tube 12 (see FIGS. 5, 6 and 7). Each tube 12, 18 also includes radiopaque strips 19 in the tube wall. The strips 19 allow radiographic confirmation of the position of the tubes 12, 18 in the patient P.

As best shown in FIGS. 2A and 5, a constriction ring 20 is provided in first passageway 14 adjacent the intubation end of the outer tube 12. The constriction ring 20 forms a portion of reduced diameter in the passageway 14. An annular engaging band 22 is formed adjacent the proximal end of the feeding tube 18. The engaging band 22 forms a portion of increased diameter on the outer surface of the feeding tube 18. The band 22 is sufficiently large to form a driving piston for the tube by pressurized fluid from syringe Y (note arrow A in FIG. 4 and also see FIG. 6). The band 22 is intercepted at the end of travel and retained by the ring 20 when fully extended (see FIG. 5).

Thus, when the feeding tube 18 is fully extended, the proximal end of the feeding tube is retained within the end of the passageway 14 through the engagement of the constriction ring 20 with the band 22. Further, as should be appreciated from viewing FIG. 5, the extending of the feeding tube serves to completely open the ports 24 in the wall of the first passageway 14 adjacent the intubation end of the sump tube 12. In order to provide this full extension, it may be necessary to slightly withdraw the tube 12 upwardly after the pressurized fluid from syringe Y begins to escape from the ports 24. The feeding tube 12 then rests in an orderly coil in the stomach, and of course, the position can be monitored by radiographic equipment during this entire process. The outer tube is then positioned in the optimum position in the stomach for the sump operation. The ports 24 allow the passage of material from the stomach through the passageway 14 during the sump operation.

The distal end of the feeding tube 18 includes a weighted tip 26 of, for example, encapsulated tungstun. The weighted tip 26 resists feeding tube aspiration and promotes the positioning of the tip 26 of the feeding tube 18 toward the pyloric valve leading from the stomach to the duodenum. Thus, the feeding tube 18 is advantageously positioned for smooth and effective movement from the stomach to the duodenum immediately with the return of any gastric emptying. Ports 28 provided adjacent to tip 26 allow the passage of nutritional support directly to the duodenum from the feeding tube 18.

The feeding ports 28 are preferably sufficiently restricted to allow a relatively slow, controlled feeding action (note relative size of ports 24, 8 in FIG. 5). This restricted size also insures that during the extension of the tube 18 by fluid pressure (see FIGS. 4–6), there is sufficient back pressure above the band 22 to generate the driving action.

In order to decompress the stomach of a patient P and initiate the sump function, the intubation apparatus 10 is introduced through the nose N of the patient P and guided past the trachea down the esophagus into the stomach S (see FIG. 3). The first passageway 14 is then connected to a source of fluid pressure, such as a syringe Y to extend the feeding tube 18, as described above (see FIG. 6). Ambient pressure is maintained through passageway 16. The syringe Y is then removed from the tube 12 and a suction source for drawing material from the stomach S through ports 24 and up the passageway 14 of sump tube 12 is provided. For example, the suction source may be the same emptied syringe Y, operated in reverse, of course. During the provision of this negative pressure to the patient, the second passageway 16 again maintains ambient pressure, this time by acting as an air in-flow lumen; that is allowing the passage of air from the vent tube extension 16a to the stomach S. The air from the second passageway 16 prevents the walls of the stomach from collapsing and being drawn into the ports 24 in first passageway 14 adjacent the intubation end of sump tube 12. Thus, the venting of air also assures that the ports 24 remain open for the passage of material from the stomach.

As pointed out above, with the apparatus of the present invention, the feeding tube 18 is immediately extended after intubation and thereafter the sump function may commence. As shown in FIG. 5, extending the feeding tube 18 does serve to completely open the ports 24 of the first passageway 14.

With the feeding tube 18 fully extended it simply remains coiled in the stomach S (see FIG. 6) for eventual movement into duodenum D for direct enteral feeding as soon as gastric emptying renews (see FIG. 7). This allows a savings in time of as many as five days from traumatic injury to enteral feeding. Advantageously, the early post-injury feeding made possible by the intubation apparatus 10 of the present invention is a positive factor significantly affecting the outcome of the treatment.

It should also be realized that the intubation apparatus 10 may be used to provide lavage function for the patient in the event a gastrointestinal bleed is manifest. In such an instance, the stomach is irrigated, for example, with antacids and/or iced saline solution that is injected through the first passageway 14 of the tube 12. The solution passes from the passageway 14 into the stomach through the ports 24. The mixture can then be removed by a follow-up sump operation; the passageway 16 and extension 16a maintaining the ambient pressure under all conditions.

To summarize the method of use, the tube 12 is first introduced through the nose N of the patient P. During introduction, it is carefully guided and monitored utilizing the weighted tip 26 to advantage. Next, in order to extend the feeding tube 18 (see FIGS. 4 and 6); a syringe Y is coupled to the proximal end of the passageway 14.

A fluid is injected under pressure to force the feeding tube 18 from the passageway 14. Once the feeding tube 18 is completely extended with the band 22 engaging the constriction ring 20, the ports 24 of sump tube 12 are completely opened for maximum sump action. The weighted tip 26 of the feeding tube 18 promotes movement of the feeding tube toward the pyloric valve, duodenum and into the jejunum during the time the tube is being extended. Thus, once gastric emptying renews, the feeding tube is perfectly positioned for advancement into the duodenum for enteral feeding.

Upon the return of gastric emptying which eliminates the need for the sump, the tip 26 moves immediately down the duodenum into the jejunum past the ligament of Treitz. Upon radiographic confirmation of the proper positioning of the feeding tube in the jejunum, enteral feeding is ready to commence. Feeding requires the complete withdrawal of the sump tube 12 from the nose of the patient (see FIG. 7). Since the band 22 of feeding tube 18 engages the constriction ring 20 of the first passageway 14 of sump tube 12, the proximal end of the feeding tube is withdrawn with the sump tube so as to extend from the nose. The sump tube 12 is then severed below the passageway 16, that is just above the constriction ring 20 (see FIG. 7) and the severed portion is discarded. Nutritional support media is then supplied through syringe Y and passes down the silicone feeding tube 18 to provide the enteral feeding through the ports 28 in the duodenum. Preferably, the tip 26 and the adjacent ports 28 are located just beyond the ligament of Treitz.

In summary, numerous benefits have been described which result from employing the concepts of the present invention. Specifically, the intubation apparatus 10 of the present invention may be used to provide sump, lavage and feeding functions to a patient P with only a single intubation. Thus, the apparatus of the present invention eliminates a significant disadvantage found in the prior art of enteral feeding wherein a second, separate intubation of the feeding tube is required following removal of the sump tube. This additional intubation characteristic of the prior art greatly reduces patient comfort and safety through further nasopharyngeal irritation and possible further traumatization of the protective surfaces of the trachea and esophagus possibly leading to bacterial infection and or bleeding.

Further, the present invention provides for a feeding tube 18 that may be extended into the stomach at the initiation of the sump function. Therefore, the feeding tube 18 is in position and begins to move from the stomach into the duodenum, then on into the jejunum as soon as there is any resumption of gastric emptying. Advantageously, this reduces the amount of time between serious injury and the administration of enteral feeding over the conventional treatment using two separate intubations. As many as five days may be saved. Such a savings of time may be essential to the recovery of the patient, particularly, if the patient is suffering from a head injury as early nutrition in such an instance is essential.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the ports 24 and 28 may initially be filled with a digestible or dissolvable material. The material serves to block the ports during intubation and prevents the escape of pressurized fluid so as to provide smooth and complete extension of the feeding tube 18 with the syringe. Shortly after intubation, the material breaks down to open the ports for sump and feeding functions. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. An intubation apparatus for providing lavage, sump and enteral feeding functions and the like for a patient, comprising:
   a first tube including at least one passageway and having a first end for introduction into the patient;
   port means in the passageway adjacent the first end of the first tube; and
   a second tube having a proximal and a distal end, said second tube being received within the passageway of said first tube and movable between an intubation position wherein said second tube is contained within said first tube and an extended position wherein the second tube extends from the first tube so as to open the port means within the passageway for sump operation;
   said first tube including a constriction means between said port means and said first end and said second tube including means adjacent the proximal end for engaging said constriction means so as to retain the proximal end of said second tube within the passageway of said first tube when said second tube is in the extended position.

2. The apparatus of claim 1, wherein said constricting means comprises a ring of reduced diameter within said first tube.

3. The apparatus of claim 1, wherein said engaging means comprises a band of increased diameter around said second tube that acts as a piston for extending the second tube from the first tube with pressurized fluid.

4. The apparatus of claim 1, wherein said second tube includes a weighted tip adjacent the distal end for aiding in positioning the distal end of the second tube, when in the extended position, within the duodenum of the patient.

5. The apparatus of claim 4, wherein said tip is of encapsulated tungstun.

6. The apparatus of claim 1, wherein said second tube is a silicone feeding tube including ports adjacent the distal end.

7. The apparatus of claim 1, wherein said first and second tubes include spaced radiopaque strips, thereby enabling viewing of the position of the tubes within the patient.

8. The apparatus of claim 1, wherein said first tube includes a second passageway extending substantially along the length of said first mentioned passageway and providing air flow to maintain ambient pressure adjacent the first end of said first tube.

9. A method of providing lavage, sump and feeding functions to a patient with a single intubation, comprising the steps of:

introducing a multiple function intubation apparatus through the nose of the patient and guiding the apparatus into the stomach;

extending a feeding tube from the apparatus to open ports in an outer tube of the apparatus allowing lavage and sump function, said feeding tube remaining coiled in the stomach until gastric emptying advances the feeding tube into the duodenum;

withdrawing the outer tube and proximal end of the feeding tube from the nose of the patient while maintaining the distal end of the feeding tube in the duodenum allowing enteral feeding function.

10. The method of claim 9, wherein said extending step includes the step of injecting a pressurized fluid into the outer tube to force the feeding tube into an extended position.

* * * * *